United States Patent
Ehrnsperger et al.

(10) Patent No.: US 6,683,229 B1
(45) Date of Patent: Jan. 27, 2004

(54) DISPOSABLE ABSORBENT ARTICLE STORING LIQUID IN A CONSTANT PATTERN

(75) Inventors: Bruno Johannes Ehrnsperger, Frankfurt (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/857,742

(22) PCT Filed: Jun. 29, 1999

(86) PCT No.: PCT/US99/14647

§ 371 (c)(1),
(2), (4) Date: Jun. 8, 2001

(87) PCT Pub. No.: WO01/10371

PCT Pub. Date: Feb. 15, 2001

(30) Foreign Application Priority Data

| Jun. 29, 1998 | (WO) | PCT/US98/13449 |
| Jun. 29, 1998 | (WO) | PCT/US98/13497 |
| Jun. 29, 1998 | (WO) | PCT/US98/13521 |
| Jun. 29, 1998 | (WO) | PCT/US98/13523 |

(51) Int. Cl.$^7$ .............................................. A61F 13/15
(52) U.S. Cl. ................ 604/368; 604/367; 604/385.101; 604/378
(58) Field of Search .................................. 604/368, 367, 604/378, 385.01, 385.101

(56) References Cited

U.S. PATENT DOCUMENTS

| 5,422,169 | A | * | 6/1995 | Roe ............................. 428/212 |
| 5,490,846 | A | * | 2/1996 | Ellis et al. ................... 604/366 |
| 5,849,002 | A | * | 12/1998 | Carlos et al. ................ 604/378 |
| 5,879,343 | A | * | 3/1999 | Dodge, II et al. ........... 604/378 |
| 5,913,850 | A | * | 6/1999 | D'Alessio et al. .......... 604/378 |
| 6,037,518 | A | * | 3/2000 | Guidotti et al. ............. 604/378 |
| 6,465,712 | B1 | * | 10/2002 | Matthews et al. ........... 604/378 |

* cited by examiner

*Primary Examiner*—Weilun Lo
*Assistant Examiner*—Jacqueline Stephens
(74) *Attorney, Agent, or Firm*—Eric T. Addington; Caroline Wei-Berk; Ken K. Patel

(57) ABSTRACT

The present invention provides an absorbent article such as a diaper, a training pant, an adult incontinence article, a bed mat, or the like which is capable of evenly storing urine in a first storage region and in a second storage region. In particular, the fraction of the amount of liquid stored in the first storage region to the amount of liquid stored in the second storage region remains relatively unchanged over a wide range of loadings of the article. The present invention further provides a process for handling urine in the absorbent article which comprises a step of storing liquid in a first storage region and of storing, liquid in a second storage region such that the ratio of the amount of liquid stored in the first storage region to the amount of liquid stored in the second storage region remains relatively constant over a wide range of loadings of the article.

11 Claims, No Drawings

DISPOSABLE ABSORBENT ARTICLE STORING LIQUID IN A CONSTANT PATTERN

FIELD OF THE INVENTION

The present invention relates to absorbent articles such as diapers, training pants, adult incontinence articles, bed mats, and the like. In particular, the present invention relates to those absorbent articles which store urine by means of either capillary or osmotic pressure.

BACKGROUND

Absorbent articles such as diapers, training pants, adult incontinence articles, bed mats, and the like are well known in the art and are frequently used for example for babies, toddlers, incontinent persons, and bed-ridden persons.

It has been recognized in the prior art that storing acquired urine close to the respective body exit may bear inherent disadvantages. The human urethra is located almost in between the legs of the human being. Hence, storage in particular of larger gushes of urine close to the urethra would lead to increased bulk in between the legs of the wearer. Increased bulk, of course, limits the mobility of the wearer and thus is uncomfortable. It is therefore desirable to store the acquired urine away from the point of acquisition.

To minimize the caliper over the entire storage area and to optimize material usage within that storage region, it is further desired to distribute the liquid as easily as possible over the storage area.

PCT patent publication WO 98/22067 (Matthews et al.) provides a personal care product in which the ratio of the amount of liquid stored in the center region to the amount of liquid storage in at least one of the end regions 30 minutes after an insult is less than 5:1. Whilst a small part of the acquired liquid is transported outside of the acquisition region, it has been failed to recognize how the acquired liquid should be distributed with in the storage region.

PCT patent application WO 98/43578 (LaVon et al.) provides an absorbent article comprising absorbent core with a crotch region and at least one waist region whereby said crotch region has a lower ultimate liquid storage capability than the waist region. The article further has an improved liquid handling performance such as an acquisition rate of at least 0.6 ml/s in the fourth gush.

Hence, it is an object of the present invention to overcome the problems of the prior art absorbent articles.

It is a further object of the present invention to provide the absorbent article which transports acquired liquid out of the acquisition region and distribute the acquired liquid within the storage region.

It is a further object of the present invention to provide an absorbent article which stores the acquired liquid in a constant fill pattern outside the acquisition region.

SUMMARY OF THE INVENTION

The present invention provides absorbent article comprising an acquisition region, a first storage region being separate from said acquisition region, and a second storage region being separate from said acquisition region, said second storage region being symmetrically different from said first storage region. The article has a total design capacity, said first storage region having a capacity of at least 10% of said total design capacity, said second storage region having a capacity of at least 10% of said total design capacity. The absorbent article according to the present invention is characterized in that said article has a fill pattern difference of less than 30% according to the fill ratio test disclosed herein.

The present invention further provides a process for storing urine in an absorbent article. The article has an acquisition region, a first storage region being separate from said acquisition region, and a second storage region being separate from said acquisition region and being symmetrically different from said first storage region. The process for storing body fluids comprises the steps of:

acquiring liquid into said article at said acquisition region, the amount of liquid acquired into said acquisition region being a fraction A of the total design capacity of said article for managing urine, storing liquid in a first liquid storage region, the amount of liquid being stored in said first liquid storage region being a fraction B1 of said acquired liquid, said fraction B1 being at least 10%, storing liquid in a second liquid storage region, the amount of liquid being stored in said second liquid storage region being a fraction B2 of said acquired liquid, said fraction B2 being at least 10%.

The process of the present invention is characterized in that for any value of said fraction A between 20% and 80% the ratio of B1/B2 differs by less than 30% from the ratio of B1/B2 for a fraction A of 20%.

DETAILED DESCRIPTION OF THE INVENTION

The present invention is described in the following by means of a variety of different embodiments and by means of a variety of different features. Further embodiments of the present invention may be obtained by combining features of one embodiment with features of another embodiment disclosed herein and/or with other features disclosed herein. These further embodiments are considered to be implicitly disclosed herein and hence form part of the present invention. It will be apparent to the skilled person that combinations of certain features may lead to non-functional articles not forming part of this present invention.

It is one aspect of the present invention to provide a process for storing urine in a article for managing urine in a constant storage pattern. It is another aspect of the present invention to provide a article for managing urine.

The absorbent article of the present invention is capable of storing urine in a constant pattern. In other words, the absorbent article of the present invention is capable of filling different storage regions with a constant filling ratio. For the purposes of the present invention, this capability is quantified by the Fill Ratio Test defined hereinafter. The absorbent article according to the present invention has a fill pattern difference of less than 30% according to the fill ratio test disclosed herein, preferably a fill ratio difference of less than 20%, more preferably a fill ratio difference of less than 10%, most preferably a fill ratio difference of less than 5%.

Preferably, the absorbent article of the present invention further rapidly acquires urine in an in-use configuration. For the purposes of the present invention, this capability is quantified by the curved acquisition test disclosed hereinafter. The absorbent article according to the present invention has a liquid acquisition rate in the fourth gush of at least 2 milliliters per second, preferably a liquid acquisition rate in the fourth gush of at least 2.5 milliliters per second, more preferably a liquid acquisition rate in the fourth gush of at least 3 milliliters per second, most preferably a liquid acquisition rate in the fourth gush of at least 4 milliliters per second.

The entire absorbent article of the present invention is intended to be worn by a wearer such that the wearer retains his mobility during use of the article of the present invention. In some embodiments of the present invention, the absorbent article of the present invention comprises an attachment means which is unitary with the article. The term "unitary" as used herein indicates that the attachment means is joined to the absorbent article and that the attachment means is not intended to be separated from the article during use of the article. The attachment means is intended to hold the absorbent article of the present invention around the lower torso of the wearer during use. Suitable attachment means such as for example adhesive tapes, mechanical fasteners, garment like articles, and the like are well known in the art. Alternatively, the absorbent article of the present invention may be attached to the lower torso of the wearer by an attachment means which is not unitary with the article such as for example a pant.

It is further desirable for the absorbent article of the present invention that it is sufficiently flexible to readily conform with the body of the wearer during use.

For the purpose of the present invention, a Cartesian coordinate system is defined as follows. The z—direction is defined to be perpendicular to the surface of the acquisition region at the intended loading point. The x—direction is defined to coincide with the longitudinal dimension of the absorbent article. In the case of a diaper, the x—direction runs from the front region of the article (which comes into contact with the front waist region of the wearer during use) to the back region of the article (which comes into contact with the back waist region of the wearer during use). Accordingly, the y—direction coincides with a transverse dimension of the absorbent article which runs from the left to the right of the wearer during use. It is to be understood in this context that this Cartesian coordinate system is only a truly Cartesian coordinate system when the article is in the flat out configuration. For typical in use conditions, the configuration of the article is such that x—, y—, and z—direction as defined above only form a locally perpendicular set of coordinates.

The article of the present invention has a total design capacity. The term "total design capacity" as used herein refers to the maximum volume of body liquid that the article is designed to absorb. Typically, the total design capacity equals the combined capacity of all storage members under typical usage conditions. If the storage members can not be identified, then the total design capacity may be determined by the Capacity Dunk Test defined hereinafter. The total design capacity is also related to the amount of body liquid exudated by the user of the article during the intended usage period.

The article for managing body liquids of the present invention comprises at least one acquisition region. The term "acquisition region" as used herein refers to that region of the article which comprises the intended loading point of the article. The term "loading point" as used herein is that point or region of the article which is intended to be positioned closest to the exit of the urethra of the wearer during use. Typically, the acquisition region is dimensioned such that it allows for variation of the mutual relative positioning of the respective body exit with respect to the article. The acquisition region may also comprise means for intermediate storage of the acquired liquids. Generally, the acquisition region extends over at least a third of the longitudinal dimension of the absorbent article, extends over the entire transverse dimension of the absorbent article, and extends over the entire caliper of the absorbent article. Preferably, the acquisition region is positioned within the absorbent article such that the intended loading point is centered with respect to the acquisition region.

The absorbent article of the present invention comprises at least one waist region. The term "waist region" as used herein refers to those regions forward and/or backward of the above mentioned acquisition region of the absorbent article. Accordingly, the waist region may account for up to two thirds of the longitudinal dimension of the absorbent article. Like the acquisition region, the waist region extends over the entire transverse dimension of the absorbent article and extends over the entire caliper of the absorbent article. The waist regions are typically intended to be positioned in close proximity to the front waist region or the back waist region respectively of the wearer during use.

The absorbent article of the present invention comprises a first storage region and a second storage region. The term "storage region" as used herein refers to those regions of the article which are intended to ultimately store the urine. Typically, these regions exhibit a higher suction than for example the acquisition region of the article. Accordingly, the combination of all storage regions will contain most of the acquired liquid in the limit of long wearing times if the article is loaded with less than 75% of its total design capacity. Whilst first storage region and second storage region of the may be regions of one larger storage region, first storage region and second storage region of the article of the present invention are symmetrically different from each other.

The term "symmetrically different" refers to a first storage region and a second storage region, both of these regions being comprised in another storage region. In this context, first storage region and second region are defined in the following way:

I. A storage region S having a total capacity of at least 20% of the total design capacity of the absorbent article is selected (this could for example be the front or the back waist region) which is connected in the x,y-dimension. Connected in the x,y-dimension means that in the x-y plane (2 dimensional) there exists a continuous curved line that connects the projections of any points A and A' that are part of region S onto the x,y-plane without leaving the projection of region S onto the x,y-plane.

II. The above region S is divided into two sub regions S1 and S2 which satisfy the following requirements:
  A. The storage capacity of S1 is substantially equal to the storage capacity of S2.
  B. The storage capacity of S1 is more than 40% of the storage capacity of S.
  C. Regions S1 and S2 are connected in the x,y-dimensions.
  D. Both regions do not overlap in the z-direction.
  E. Region S1 is closer to the acquisition region than region S2. In this context, the term "closer" refers to the distance of the capacity centerpoint of region S1 being at least 3 cm closer to the loading point than the capacity centerpoint of region S2. The capacity center point is given by the center of gravity of the liquid stored in the region when the article is fully loaded via the capacity dunk test.

It is to be understood in this context that these regions are defined in a purely geometric way. In particular, there is no need that the positioning of these regions is reflected in the structure of the article such as by a change in material.

Optionally, the absorbent article according to the present invention may comprise a liquid handling member which is intended to transport urine from the acquisition region to a waist region and potentially to a storage member positioned inside a waist region.

The process for handling urine according to the present invention comprises a step of acquiring urine into the article of the present invention at the acquisition region of the article. Typically, the step is triggered by the disposal of urine onto the acquisition region of the article by the wearer. Preferably, the acquisition rate of the article during the step is sufficiently high to prohibit liquid runoff from the article which subsequently may lead to leakage and to minimize skin contact with the urine. During this acquisition step, a certain volume of urine is acquired into the article which is a fraction A of the total design capacity of the absorbent article.

The process of the present invention further comprises a step of storing a first portion of the acquired liquid in the first storage region and a second portion of the acquired liquid in the second storage region. The fraction of the acquired liquid which is stored in the first storage region is referred to as B1 whereas the fraction of the acquired liquid which is stored in the second storage region is referred to as B2. In the process of the present invention, fractions B1 and B2 are at least 10 percent, preferably at least 20 percent, more preferably at least 30 percent, most preferably at least 40 percent.

During the process of the present invention the ratio of B1/B2 for any value of fraction A between 20 percent and 80 percent differs by less than 30 percent from the ratio of B1/B2 for a fraction A of 20 percent, preferably differs by less than 20%, more preferably differs by less than 10%, most preferably differs by less than 5%. In other words, the ratio of the amount of liquid stored in the first liquid storage region to the amount of liquid stored in the second liquid storage region remains relatively constant over a wide range of different loadings of the absorbent article. Hence, the acquired liquid is distributed evenly between first storage region and second storage region such that the caliper increase over the storage region as a whole can be minimized and the material can be utilized most efficiently.

Optionally, the process of the present invention may comprise a step of transporting at least a portion of the acquired liquid from the acquisition region to the first storage region and/or to the second storage region. This process step may be carried out by the optional liquid handling member of the absorbent article of the present invention.

The absorbent article according to the present invention is capable of storing acquired liquid evenly in the first storage region and in the second storage region. This allows that the caliper increase or the storage region as a whole can be minimized and that the material of the storage regions can be utilized most efficiently. For the purpose of this invention, this capability is quantified by the fill ratio test defined hereinafter. The absorbent article according to the present invention has a fill ratio difference of less than 10 percent according to the fill ratio test disclosed herein, preferably of less than eight percent, more preferably of less than six percent, most preferably of less than four percent.

Optionally, the process for handling urine according to the present invention comprises a step of attaching the absorbent article to the lower torso of the wearer. During the step, the attachment of the article is achieved by means of the attachment means unitary with the article. The step may be carried out by the wearer himself or the step may be carried out by a caregiver. The purpose of the step is to align urethra with the acquisition region of the article.

In the following, a suitable embodiment of the liquid handling member will be described. The liquid handling member is assembled from an open celled foam material which is completely enveloped by a membrane. A suitable membrane material is available from SEFAR of Ruschlikon, Switzerland, under the designation SEFAR 03-20/14. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid handling member, it may also be required to choose similar materials with slightly different properties. After assembly, the liquid handling member is activated by immersing the liquid handling member in water or in synthetic urine until the liquid handling member is completely filled with liquid and until the membranes are completely wetted with liquid. After activation, a part of the liquid inside the liquid handling member may be squeezed out by applying an external pressure to the liquid handling member. If the activation of the liquid handling member was successful, the liquid handling member should not suck air.

The particular geometry of the liquid handling member of the present invention can be varied according to the specific requirements of the intended application. If, for example, the liquid handling member is intended to be used in an absorbent article the liquid handling member may be defined such that its zone of intended liquid acquisition fits between the legs of the wearer and further that its intended liquid discharge zone matches the form of the storage member associated to it. Accordingly, the outer dimensions of the liquid handling member such as length, width, or thickness may also be adapted to the specific needs of the intended application. In this context, it has to be understood, however, that the design of the outer form of the liquid handling member may have an impact on its performance. For example, the cross section of the liquid handling member directly impacts on its liquid flow rate.

For application of the liquid handling member in an absorbent article according to the present invention, the liquid handling member may be combined with a storage member. The term "liquid storage member" refers to an article which is capable of acquiring, distributing and/or storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. A suitable absorbent gelling material is ASAP400 available from Chemdal Ltd., United Kingdom. Further examples of suitable superabsorbent polymers, often also referred to as "hydrogen forming polymer" or "absorbent gelling material", are described in U.S. Pat. No. 5,562,646

(Goldman et al.), issued Oct. 8, 1996 and U.S. Pat. No. 5,599,335 (Goldman et al.), issued Feb. 4, 1997.

In order to pick up the liquid discharged from the liquid handling member, the storage member may be placed in direct liquid communication with the intended liquid discharge zone of the liquid handling member.

Other liquid handling members suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications co-filed with the present application entitled "High flux liquid transport members comprising two different permeability regions" (P&G case CM1840MQ) filed in the name of Ehrnsperger et al., "Liquid transport member for high flux rates between two port regions" (P&G case CM1841MQ) filed in the name of Ehrnsperger et al., "Liquid transport member for high flux rates against gravity" (P&G case CM1842MQ) filed in the name of Ehrnsperger et al., "Liquid transport member having high permeability bulk regions and high bubble point pressure port regions" (P&G case CM1843MQ) filed in the name of Ehrnsperger et al. All of these documents are enclosed herein by reference.

In one embodiment of the present invention, the liquid handling member of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules a according to NMR (nuclear magnetic resonance) spectroscopy methods well known in the art.

In one embodiment of the present invention, the absorbent article is a disposable absorbent article such as a diaper, a training pant, a sanitary napkin, an adult incontinence article, or the like. Such an absorbent article may further comprise a liquid pervious topsheet, a liquid impervious backsheet at least partially peripherally joined to the topsheet. The absorbent article may further comprise an absorbent core which may serve as a storage member for the urine. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

METHODS

Unless stated otherwise, all methods are carried out at ambient conditions, i.e. 32+/−2° Celsius and 30–50% relative humidity.

Unless stated otherwise, the synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4

Capacity Dunk Test

This test is intended to measure the total capacity of an absorbent article.

As the first step of this test, the test specimen is completely immersed in synthetic urine for 10 minutes.

Then, the test specimen is put with its acquisition region facing the glass frit on a sufficiently large glass frit which is in direct liquid communication with a liquid reservoir filled with synthetic urine. Hence, this glass frit provides a hydrohead of about 1 mm. After thirty minutes, the test specimen is removed from the glass frit.

Finally, the total capacity of the test specimen is determined by weighing the liquid uptake of the test specimen.

Fill Ratio Test Method

This test method is intended to measure the ratio of the liquid stored in a first storage member of the device to be tested to the liquid stored in a second storage member of the device. Therefore, the ratio of liquid amounts in the two storage members is measured shortly after the liquid has been acquired at the loading point of the device. The test is suitable for devices which comprise a first storage member and second storage member with both storage members having a total capacity of at least 5% of the total design capacity of the device.

For the purpose of this test method, samples of the device to be tested are loaded with one or more gushes of synthetic urine. For this test, a gush is defined as having the volume of 20% of the total design capacity of the device to be tested. The gushes are disposed onto the loading point of the device in 5 minute intervals at a rate of about 5 ml/s or at the maximum rate not causing liquid to run-off whichever is lower. The 5 minute interval starts when the preceding gush is completely absorbed by the device.

For the purpose of this test method, the loading or liquid uptake of the first storage region and the second storage region of the device to be tested have to be measured separately. There exists a variety of potentially suitable test methods to determine the liquid uptake of a certain region. It will be readily apparent to the skilled person which method is the most suitable for the device to be tested. The potentially suitable methods range from very simple methods such as severing the device into its different regions and weighing its weight increase to more complex methods such as x-ray analysis and nuclear magnetic resonance spectroscopy. In x-ray analysis, the effect that the amount of energy absorbed when the device is exposed to x-rays is proportional to the amount of liquid per unit surface area contained in the device is used to determine the water content of specific regions of the device. For example, such a method is described in an article entitled "Fluid distribution: Comparison of x-ray imaging data" by David F. Ring, Oscar Lijap, and Joseph Pascente in Nonwoven World magazine, summer 1995, at pp. 65–70. Suitable x-ray systems are available for example from LIXI Inc. of Downers Grove, Ill., USA, under the designation SA-100-2 SERIES, MODEL HLA-40-440M02. The system uses Bio-scan software from Optimas. The x-ray system may for example be operated with an exposure time of two second, with a tube voltage of 50 kV, and a current of 12 mA. It is to be noted, however, that for exposure time, tube voltage, and current different values have to be chosen depending on the specific properties of the test specimen to be examined. It is also well known in the art to determine the water content of a specific region of a device by nuclear magnetic resonance spectroscopy. In all methods, particular care has to be taken that the weight of the liquid (bound liquid as well as free liquid) which is stored in either one of the regions is exactly accounted for. It is also important that only the liquid uptake is measured by comparing a loaded device with an unloaded device.

First, a first sample of the device is loaded with a first gush of synthetic urine at its loading point. The loadings of the first storage region and the second storage region of the device are measured five minutes after the gush has been absorbed completely. The loadings will be referred to as $F_1$, and $S_1$ respectively. Then, a second sample of the device to be tested is loaded with 5 subsequent gushes. The loadings of the first storage region and the second storage region of the device are measured five minutes after the fifth gush has been absorbed completely. The loadings will be referred to as $F_5$, and $S_5$ respectively.

The fill ratio $R_i$ of a sample of the device loaded with i gushes is the ratio of the loading of the first storage region to the loading of the second storage region and is given by $$R_i = \frac{F_i}{S_i}$$

The fill pattern difference D represents the relative change of the fill ratio from 20% loading to 100% loading. Accordingly, D is obtained by $$D = \frac{|R_5 - R_1|}{R_1}$$

Curved Acquisition Method

The curved acquisition test methods aims at simulating the introduction of urine into a device for managing body liquids. A similar test method is described in PCT patent application No. IB99/00741 (P&G case CM2060FQ) incorporated herein by reference.

The following describes key principles of the test:
1. The device is held in a curved configuration to more realistically simulate the position of the device on a standing or sitting wearer.
2. The realistic, vertical orientation requires that the liquid applied must be distributed against gravity.
3. The overall configuration provides key data on acquisition, distribution and storage of the liquid within the various materials thereby providing a better understanding of material properties, and their combined performance.
4. The apparatus includes a pressurized air cushion, allowing to better analyze products which have either a varying thickness throughout various parts thereof, or which exhibit a pronounced thickness change throughout the loading process.

The following description is adopted for devices for handling body liquids of the baby diaper type, and in particular for devices intended for babies in a weight range of about 9 to 18 kg. Nonetheless, the skilled person will be able to readily adopt it for other purposes, such as for other sizes, or adult incontinence applications. The test specimen is held in a curved plexiglas device which utilizes a flexible, soft air bag which is used to simulate various baby pressures between 0.69 kPa—6.9 kPa (0.1–1 psi), and the test specimen is loaded with subsequent gushes of liquid, with appropriate waiting time in between. The key result from this test is the time for the fluid of each of the gushes to penetrate into the test specimen. After the loading of the test specimen by this test, the test specimen can be used for further analysis, such as measuring the rewet, preferably by the Post Curved Acquisition Collagen Rewet Method (PCACORM) described in PCT patent application IB99/00741 (P&G case CM2060FQ), or measuring the caliper, or measuring the liquid distribution, such as by determining the load in various sections of the test specimen.

For test specimens having the above mentioned size, the standard protocol loads the test specimen four times with 75 ml+/-2 ml, at a rate of 15 ml/sec, delivered at one hour intervals. The present description refers to an automated procedure, including automatic data capturing. Of course, analogous systems can be used, such as manual recording of data, as long as the described principles are followed.

The test equipment is schematically depicted in FIG. 6 of PCT patent application No. IB99/00741 (P&G case CM2060FQ) incorporated herein by reference. The complete equipment, or preferably a multiplicity thereof for ease of replication, is placed inside a controlled condition chamber, with room temperature and humidity within the following limits:

| | |
|---|---|
| Temperature: | 32° C. ± 20 (90° F. ± 3° F.) |
| Relative Humidity: | 50% ± 10% |

If a deviation form this protocol is deemed appropriate, this must be stated explicitly in the protocol.

The Curved Acquisition Tester comprises four important parts (The size of this unit is adapted for baby diapers and may have to be adjusted accordingly for absorbent article for other intended user groups):

a) A holding unit which is essentially made of perspex/plexiglas. It has been found that suitable plates of 5 mm thickness provide sufficient strength for operating without undue deformation.

The essential part of the holding unit is a trough having an upper rectangular opening of 130 mm extending outside of the plane of drawing, and a width of 260 mm. The rectangular through has a length of about 200 mm and ends in a semi-cylindrical form having a radius of 130 mm. The holding unit has one or more means to retain the loading unit in place, here shown by a hinged lid and corresponding fixation means, such as screws. The holding unit further comprises means for stable support.

b) A loading unit comprising a liquid application means is designed to fit into the through of the holding unit, by having a rectangular section having a length of about 180 mm, and having cross-section of about 100 mm by 128 mm, ending in a semi-cylindrical section having a radius of 100 mm. The loading unit further comprises a flange, which allows to hang the unit into the trough by being larger than said trough opening, and which also prevents the loading unit to be pushed out of the trough by being hold by said lid. The clearance for the vertical movement of the loading unit is about 4 cm. The total loading unit is made from the same material as the holding unit, and can have a weight of about 1 kg, including the liquid application means.

c) The liquid application means comprises a plexiglas tube having an inner diameter of 47 mm, and a height of about 100 mm. It is firmly affixed to a circular opening having a diameter of about 50 mm through the loading unit, positioned centered around the lowermost point of the semi-cylindrical portion. The opening of the tube is covered by a open mesh (such as of wire mesh with openings of about 2 mm separated by threads of 1 mm), so as to be flush with the opening of the loading unit. A 6 mm diameter flexible tube, such as Norpren A60G (6404-17), available from Cole Parmer Instrument Company, IL, US, is connected to a test fluid metering pump, such as Digital Pump, Catalog, by No. G-07523-20, having a Easy-Load Pump Head, No. G-07518-02, both by Cole-Parmer Instrument Company, IL, US, with a pump control unit to allow start and stop of the pump based upon electrical signals. Two electrodes are positioned at two opposite points just inside the mesh at the lower end of the plexiglas tubing, to be able to detect interruption of the electric current through the electrolyte fluid, once the tube is being emptied. The electrodes are connected via cable to a time signal measuring unit.

d) A pressure generating means comprises a flat, flexible air cushion, such as generally available for medical purposes (blood pressure measurement), having an uninflated dimension of 130 mm by 600 mm, which can be inflated by means of a hand pump and a valve with a pressure recording device, which can be connecting to an electrical transducer so as to provide an electrically recordable signal corresponding to the pressure. This system is designed to operate at pressures of up to 6.89 kPa (1 psi), and is set for the standard procedure to 2.07 kPa (0.3 psi).

e) Optionally, the apparatus can comprise an automatic control unit, such as a suitable computer control unit, connected to the pump control unit, the timer and the pressure recorder which also can operate several measuring units in parallel. Suitable software is for example LabView® by National Instruments, Munich, Germany. A complete test equipment can be delivered by High Tech Company, Ratingen/Germany, D64293 Darmstadt.

Steps for Setting Up the Acquisition Equipment

1) Calibration of pump: before starting the experiment, the pump should be calibrated to ensure a flow rate of 75 ml per 5 seconds. If necessary, tubing should be replaced.
2) Preparation and thermal equilibration of test fluid;
3) Positioning of the cushion into the trough without folds or creases;
4) Weighing of the entire device to be tested to the nearest 0.01 g on a top loading balance. Marking of the loading point onto the test specimen with a pen. Positioning and fixation (such as by suitable adhesive tape) of the test specimen to the loading unit, such that the liquid receiving surface is oriented towards the loading unit (and hence the backsheet towards the cushion), so as to have the opening aligned with the loading point of the device. The device is then positioned onto the curved loading unit without cutting the leg elastics or other elastic, if present, with the marked loading point located under the center of the tube, and attached to the loading unit by suitable attachment means, such as tape. Generally, the configuration of the device should resemble a typical in use configuration as close as possible. The device is then positioned together with the loading unit into the tester, and the electrode cables are connected.
5) The lid is closed, and fixed with screws.
6) The cushion is then inflated to the desired pressure, i.e. 2.07kPa (0.3psi), thereby pushing the loading unit against the lid, and thus exerting the pressure on the test specimen.
7) The end of the flexible tube is positioned such that it directs to the center of the opening, and extends about 5 cm (2 in) into the tube.
8) The liquid pump is started for the preset time (i.e. 5 seconds), and at the same time acquisition time timer.
9) Upon emptying of the Plexiglas tube the electrodes provide a signal stopping the acquisition time timer, upon which the waiting time is started at the timer for 5 minutes.
10) The loading cycle (step 7 and 8) is repeated to a total of four times.

RESULTS

Upon finishing of the above cycle, the respective acquisition rates can be calculated for each "gush" by dividing the load per gush (i.e. 75 ml) by the time in seconds required for each gush. (If the acquisition rates are getting close to the liquid delivery rates (i.e. 15 ml/sec), test conditions can be changed and respectively recorded.)

What is claimed is:

1. An absorbent article, said article comprising an acquisition region, a first storage region being separate from said acquisition region, and a second storage region being separate from said acquisition region, said second storage region being symmetrically different from said first storage region, wherein said article has a fill pattern difference of less than 30% according to the fill ratio test disclosed herein.

2. An absorbent article according to claim 1 said article further comprising a liquid transport member transporting liquids from said acquisition region to said first storage region and to said second storage region.

3. An absorbent article according to claim 2, wherein said liquid transport member is substantially geometrically saturated before the intended use of said article.

4. An absorbent article according to claim 1, wherein said article is a disposable absorbent article.

5. An absorbent article according to claim 4, wherein said article is a disposable diaper.

6. A process for storing urine in an absorbent article, said article having an acquisition region, a first storage region being separate from said acquisition region, and a second storage region being separate from said acquisition region and being symmetrically different from said first storage region said process for storing body fluids comprising the steps of acquiring liquid into said article at said acquisition region, the amount of liquid acquired into said acquisition region being a fraction A of the total design capacity of said article for managing urine, storing liquid in a first liquid storage region, the amount of liquid being stored in said first liquid storage region being a fraction B1 of said acquired liquid, said fraction B1 being at least 10%, storing liquid in a second liquid storage region, the amount of liquid being stored in said second liquid storage region being a fraction B2 of said acquired liquid, said fraction B2 being at least 10% wherein for any value of said fraction A between 20% and 80% the ratio of B1/B2 differs by less than 30% from the ratio of B1/B2 for a fraction A of 20%.

7. A process for storing urine according to claim 6 wherein said article further comprises a liquid transport member and wherein said process further comprises the steps of transporting at least a portion of said acquired liquid to said first liquid storage region transporting at least a portion of said acquired liquid to said second liquid storage region said transportation steps being carried out by said liquid transport member.

8. A process for storing urine according to claim 6, wherein a liquid handling member is substantially geometrically saturated with liquid before the first acquisition of urine into said liquid handling member.

9. An absorbent article designed to carry out a process according to claim 8.

10. An absorbent article according to claim 9, wherein said article is a disposable absorbent article.

11. An absorbent article according to claim 10, wherein said disposable absorbent article is a diaper.

* * * * *

UNITED STATES PATENT AND TRADEMARK OFFICE
CERTIFICATE OF CORRECTION

PATENT NO. : 6,683,229 B1
DATED : January 27, 2004
INVENTOR(S) : Bruno Johannes Ehrnsperger et al.

It is certified that error appears in the above-identified patent and that said Letters Patent is hereby corrected as shown below:

Title page,
Item [57], ABSTRACT,
Line 3, delete "or the like" and insert -- or the like, --.
Line 10, delete "article" and insert -- article, --.
Line 11, delete "storing," and insert -- storing --.

Column 6,
Line 8, delete "Ruschlikon," and insert -- Rüschlikon, --.
Line 66, delete " "hydrogen forming polymer" " and insert -- "hydrogel forming polymer" --.

Column 7,
Line 57, delete "2.0 g/:" and insert -- 2.0 g/l --.
Line 58, delete "Na2SO4;" and insert -- $Na_2SO_4$; --.
Lines 58 and 59, delete "(NH4)H2PO4;" and insert -- $(NH_4)H_2PO_4$; --.
Line 59, delete "CaCl2;" and insert -- $CaCl_2$; --.
Line 59, delete "ad 0.23 g/l of MgCl2." and insert -- and 0.23 g/l of $MgCl_2$. --.
Line 61, delete "6.4" and insert -- 6.4. --.

Column 10,
Line 20, delete "32° C. ± 20" and insert -- 32° C. ± 2° C. --.

Column 11,
Line 30, delete "D64293" and insert -- D-64293 --.

Signed and Sealed this

Twenty-first Day of March, 2006

JON W. DUDAS
*Director of the United States Patent and Trademark Office*